(12) United States Patent
Hartigan et al.

(10) Patent No.: US 6,915,660 B2
(45) Date of Patent: Jul. 12, 2005

(54) METHOD AND SYSTEM FOR LIQUEFACTION MONITORING

(75) Inventors: Gavin D. Hartigan, Flemington, NJ (US); David L. Ruppert, Annandale, NJ (US); Henry S. Hui, Glen Gardner, NJ (US)

(73) Assignee: The BOC Group, Inc., Murray Hill, NJ (US)

( * ) Notice: Subject to any disclaimer, the term of this patent is extended or adjusted under 35 U.S.C. 154(b) by 265 days.

(21) Appl. No.: 09/827,947

(22) Filed: Apr. 6, 2001

(65) Prior Publication Data

US 2002/0144542 A1 Oct. 10, 2002

(51) Int. Cl.$^7$ .................................................. F25J 1/00
(52) U.S. Cl. .......................... 62/606; 62/617; 73/23.2; 73/430
(58) Field of Search .................. 73/430, 23.2; 62/606, 62/617, 48.1, 115; 34/343, 403; 137/113; 141/231

(56) References Cited

U.S. PATENT DOCUMENTS

| | | | |
|---|---|---|---|
| 3,775,494 A | | 11/1973 | Carr |
| 3,868,963 A | | 3/1975 | Muellerpoths |
| 4,328,455 A | * | 5/1982 | Harding, Jr. ................ 365/149 |
| 4,893,508 A | * | 1/1990 | Friedman ................ 73/335.02 |
| 4,898,476 A | * | 2/1990 | Herrmann et al. ............ 374/28 |
| 5,359,787 A | * | 11/1994 | Mostowy, Jr. et al. ........ 34/343 |
| 5,454,256 A | | 10/1995 | Gimben et al. |
| 5,456,104 A | * | 10/1995 | Rosen ........................ 73/29.02 |
| 5,539,998 A | * | 7/1996 | Mostowy et al. ............. 34/343 |
| 5,623,426 A | * | 4/1997 | Ozawa et al. ................. 702/99 |
| 5,638,296 A | * | 6/1997 | Johnson et al. ............. 700/286 |
| 5,739,416 A | * | 4/1998 | Hoenk ........................ 73/29.01 |
| 5,775,580 A | * | 7/1998 | Sizemore et al. ......... 236/44 E |
| 5,816,704 A | * | 10/1998 | Campbell et al. ............. 374/28 |
| 5,937,894 A | | 8/1999 | Rojey |
| 6,134,805 A | * | 10/2000 | Chowdhury et al. .......... 34/403 |
| 6,499,308 B2 | * | 12/2002 | Inoue et al. ............... 62/228.3 |
| 2002/0174893 A1 | * | 11/2002 | Chowdhury et al. ........ 137/113 |

FOREIGN PATENT DOCUMENTS

| | | |
|---|---|---|
| EP | 0 631 218 A2 | 12/1994 |
| JP | 60 218527 A | 11/1985 |
| JP | 62190455 A | 8/1987 |
| JP | 06 194274 A | 7/1994 |
| JP | 11 236673 A | 8/1999 |
| JP | 2000039220 * | 2/2000 ............. F25B/1/00 |
| WO | WO 98/43051 | 10/1998 |

OTHER PUBLICATIONS

Abbot et al, Schaum's outline of theory and problems of thermodynamics, 1962, 99, McGraw–Hill.*
European Search Report for Application No. 02252359.1 dated Nov. 4, 2003.
JP 06 194274 A, Toshiba Corp, Patent Abstracts of Japan, vol. 018, No. 539 (P–1812), Oct. 13, 1994.
JP 06 218527 A, Matsushita Electric Ind Co Ltd, Patent Abstracts of Japan, vol. 010, No. 077, (M–464), Mar. 26, 1986.

(Continued)

*Primary Examiner*—Hezron Williams
*Assistant Examiner*—Rodney Frank
(74) *Attorney, Agent, or Firm*—Ira L. Zebrak (57) ABSTRACT

A method and system for liquefaction monitoring of a gas in a gas piping system in which pressure and temperature information about the gas is gathered and the liquefaction status of the gas is determined and reported.

27 Claims, 7 Drawing Sheets

OTHER PUBLICATIONS

JP 11 236673 A, Mitsubishi Electric Corp, Patent Abstracts of Japan, vol. 1999, No. 13, Nov. 30, 1999.

JP 62 190455 A, Chino Corp, Patent Abstacts of Japan, vol. 12, No. 043 (P–664), Feb. 9, 1988.

N. Verma, G. Hartigan, D. Rupert, "CIF3 and Other Low Vapor Pressure Gas Systems," Semiconductor International, Jul. 1997; 253–254, 256, 258, 260.

Francisco F. A. Martinez and Marzia S. Infantini, "Phase Behavior and Splitting Analysis: An Operational Tool in Gas Transmission and Distribution"; Proceedings of the Seventy–Seventh GPA Annual Convention; pps. 30–35; Gas Processors Association 1998, Tulsa, OK.

Australian Patent Office Written Opinion and Search Report for Application No. SG 200201814–1; mailed May 5, 2004.

* cited by examiner

METHOD AND SYSTEM FOR LIQUEFACTION MONITORING

FIELD OF THE INVENTION

The invention relates to liquefaction monitoring. More particularly, the present invention relates to a method and system for monitoring the liquefaction status of a gas in a gas distribution piping system.

BACKGROUND OF THE INVENTION

Specialty gases are often used in numerous process steps during the fabrication of advanced semiconductor devices. Gases with low vapor pressures at room temperature, are typically stored as liquids in a container, under their own vapor pressure, and many of them are very hazardous. In many instances, the process gases may have to be transported along a gas distribution or piping system to a reactor across a manufacturing facility. Changes in the ambient air around the piping system may affect the physical state of the gas inside the piping system. For example, a temperature decrease or a pressure increase may cause the gas to liquefy and result in adverse effects on the performance of the gas distribution system, including pressure fluctuations, reduced component life and in some cases, dangerous chemical reactions.

Efforts to monitor liquefaction—i.e., a change from a gaseous to a liquid state, of such gaseous materials include the use of optical devices that detect liquefaction by light scattering. However, such devices tend to be expensive and only detect liquid formation after liquefaction has occurred. Thus, the need exists for a more cost-effective method of monitoring liquefaction before it occurs.

SUMMARY OF THE INVENTION

The present invention provides generally a method and a system for monitoring the liquefaction status for a gas based on pressure and temperature information about the gas. According to one aspect of the invention, a method provides for gathering pressure and temperature information from a gas product in a gas piping system and determining the liquefaction status from the gathered information. In one embodiment, the pressure and temperature information are represented by two parameters that correlate respectively with an operating temperature and operating pressure of the gas. Based on the two parameters and reference data involving pressure and temperature for the gas, the liquefaction status of the gas is determined and reported.

According to another aspect of the invention, a system is provided for determining and reporting the liquefaction status of a gas. In one embodiment, the system comprises means for providing at least two parameters correlated respectively to an operating temperature and an operating pressure of the gas, means for providing one or more reference data sets for the gas, means for determining the liquefaction status of the gas based on the at least two parameters and the one or more reference data set, and means for reporting the liquefaction status of the gas.

In another embodiment, the system comprises at least one sensor selected from the group consisting of temperature and pressure sensors for monitoring a gas product in a gas piping system, a tolerance-level-determination engine for determining the liquefaction status of the gas product using data from the sensor, and a results-reporting engine operatively connected to the tolerance-level-determination engine for reporting the liquefaction status.

In yet another embodiment, the system comprises a tolerance-level-determination engine operatively connected to a pressure transducer in a gas piping system, a temperature data collector connected to the tolerance-level-determination engine, a results-reporting engine operatively connected to the tolerance-level-determination engine, and at least one indicator operatively connected to the results-reporting engine for indicating the liquefaction status of a gas product.

In yet another embodiment, the system comprises sensors for monitoring a pressure and a temperature of a gas product in a gas piping system, a tolerance-level-determination engine for liquefaction monitoring using data from the pressure and temperature sensors, a results-reporting engine operatively connected to the tolerance-level-determination engine, a housing enclosing the tolerance-level-determination engine and the result-reporting engine, the housing being removable from the gas piping system and at least one indicator connected to the results-reporting engine.

BRIEF DESCRIPTION OF THE DRAWINGS

The present invention can be more fully understood by reference to the following description and accompanying drawings, which form an integral part of this application.

DETAILED DESCRIPTION

Figure 1:
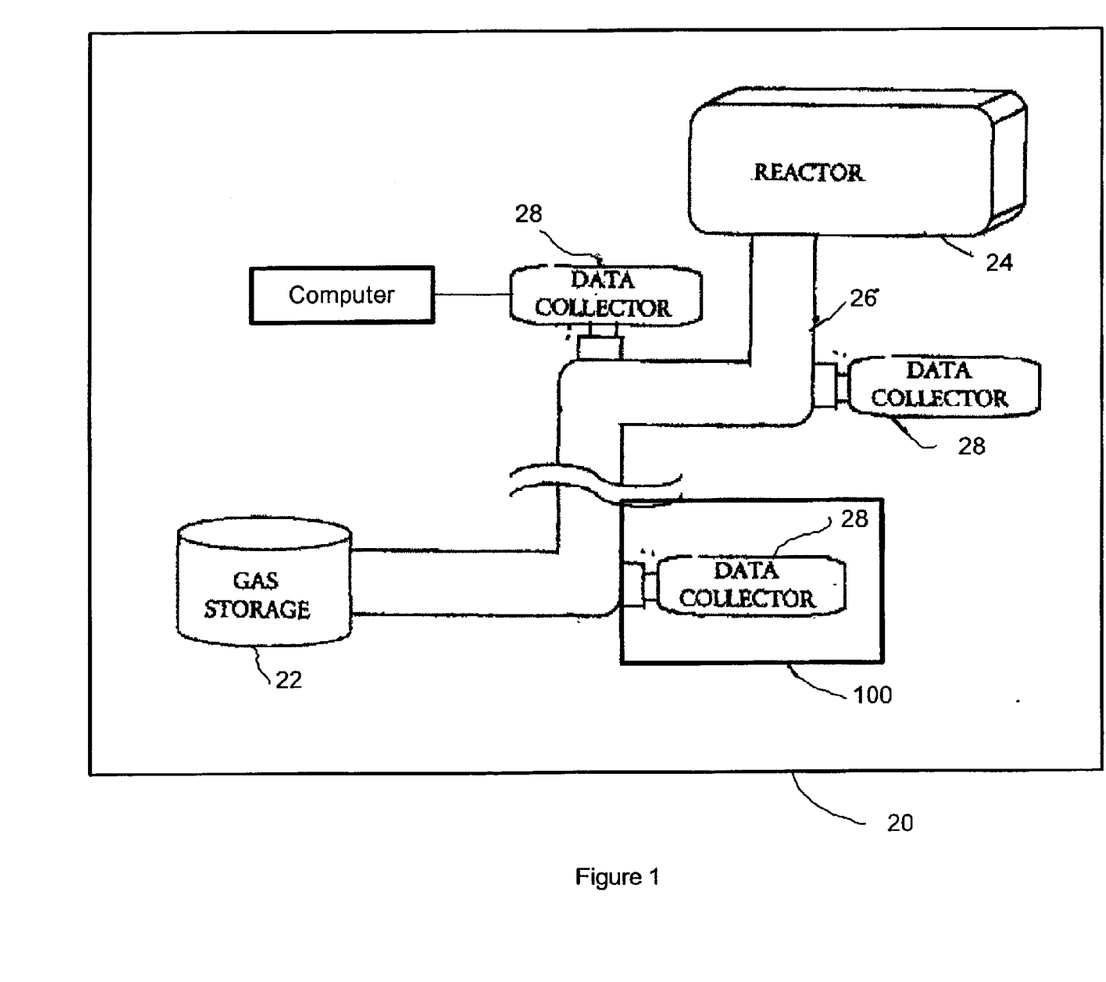
FIG. 1 is a diagram of a gas distribution system adapted for liquefaction monitoring according to the present invention.

With reference to the figures for purposes of illustration, the present invention relates to liquefaction monitoring in a gas distribution system. An exemplary gas distribution system 20 is illustrated by FIG. 1 in which a gas storage tank 22 is connected to a reactor 24 by a gas piping system 26. It will be appreciated by those skilled in the art that many different arrangements of gas distribution systems may be contemplated and the illustration of FIG. 1 is for purposes of illustration only and is not intended to be limiting.

In order to overcome the problems associated with conventional sensors for detecting liquefaction, the present invention is based upon the realization that liquefaction occurs in accordance with the fundamental thermodynamic relationships. It is therefore possible to derive information about the state of the product using the thermodynamic relationships of the product. According to one aspect of the present invention, data collectors 28 are distributed along the gas piping system 26 at sensing points for providing temperature and pressure information about the product in the gas distribution system 20. The data collectors 28 may provide such information through various means, including, but are not limited to, temperature and/or pressure sensors, manual measurements of temperature and/or pressure, estimated values of temperature and/or pressure based on measurements of other thermodynamic properties or any combination thereof. In one embodiment, a data collector 28 is incorporated as part of a liquefaction monitoring unit 100, which includes appropriate hardware (e.g., processor, computer, circuitries, among others) and software for implementing a liquefaction monitoring process along the gas piping system 26. In another embodiment, a data collector may also be connected to a processor or computer for data handling and processing. In yet another embodiment, multiple data collectors and/or liquefaction monitoring units incorporating the data collectors may be used collectively for liquefaction monitoring along the gas piping system 26.

Figure 2:
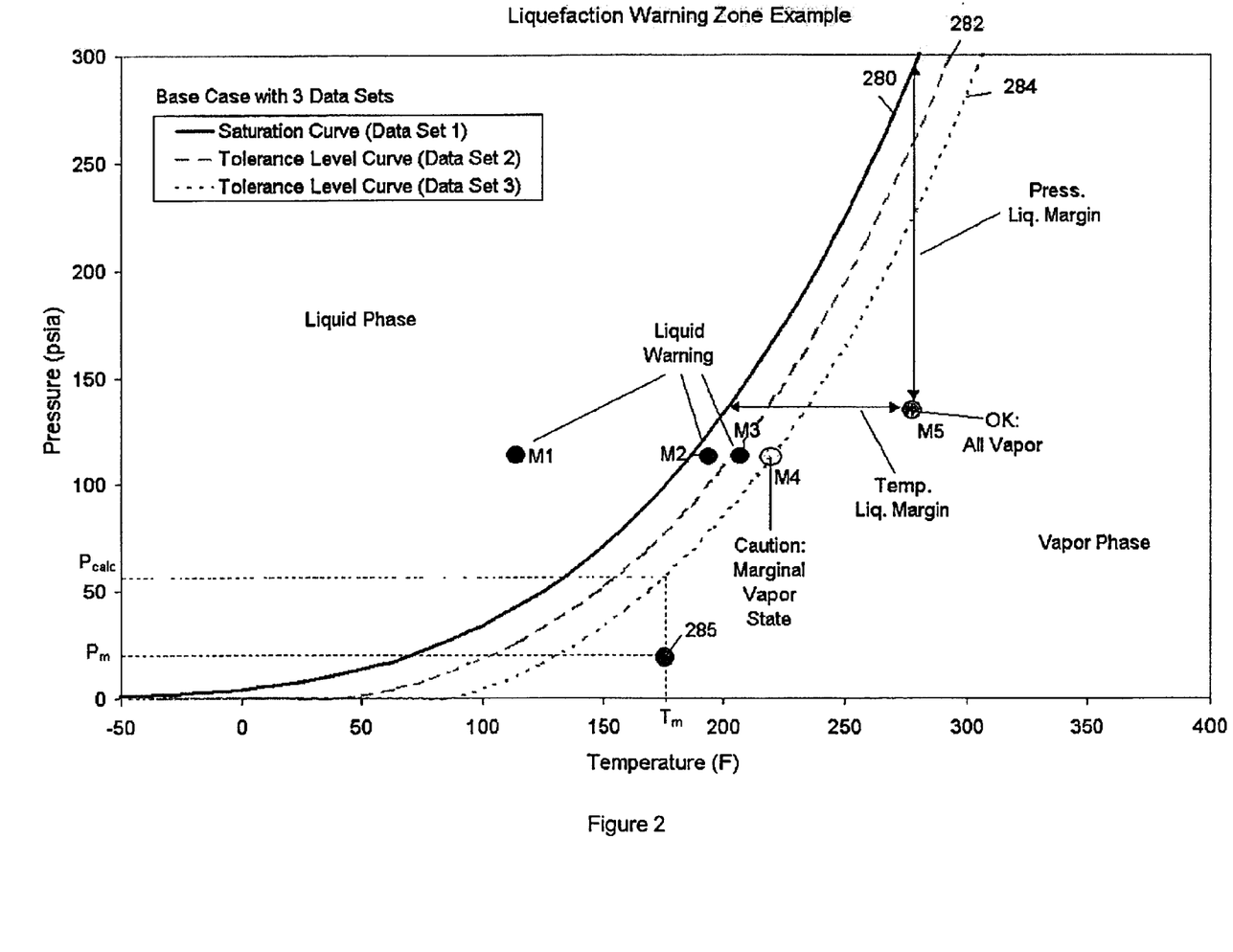
FIG. 2 is a graph illustrating the concept of tolerance levels for liquefaction monitoring.

The process of determining liquefaction is based on input parameters such as temperature and pressure or at least two thermodynamic properties provided by the data collectors 28. In one preferred embodiment, each step of the process is carried out through a series of electronic components, which may include sensors, circuitry, microprocessors, various computer-readable media, memory or storage devices, among others, that can be combined as a self-contained sensor unit for easy installation in a gas distribution piping system and thus allows continuous liquefaction monitoring at the sensing points. The liquefaction monitoring process involves calculating a theoretical state of the product from accurate saturation property data that are available for a given gas, and comparing the input parameters with the theoretical state to determine the product state or liquefaction status in the piping system. FIG. 2 is a pressure vs. temperature graph for illustrating liquefaction monitoring of a gas product according to embodiments of the present invention. As shown in FIG. 2, one theoretical state of the product may be represented by a saturation data curve 280, also known as a characteristic phase envelope. The saturation data curve may be generated from a variety of approaches that are known to one skilled in the art, including, but not limited to, calculations from equation of states, molecular simulation, empirical or experimental data, or any combinations thereof. A series of tolerance level curves 282, 284 representing Data Sets 2 & 3 in FIG. 2 are derived relative to the saturation data curve 280. Product state, as defined by input parameters or operating temperature and pressure, for example, is then compared with these tolerance curves 282 and 284. Based on the location of the product state with respect to these tolerance curves 282 and 284, different liquefaction warnings may be reported by audio and/or visual indicators. Thus, the present invention provides a liquefaction monitoring unit to quickly assess the product state in the gas piping system and to indicate to operational personnel possible liquefaction status of the product, e.g., when liquefaction is occurring, liquefaction is imminent, or no liquefaction is occurring. The present invention will operate satisfactorily when configured to report at least one of the operational liquefaction states. However, unless otherwise desired to have less tolerance levels, at least three tolerance levels are currently preferred. It is understood that such preferences are application dependent such that more or less tolerance levels may be desired when the device is used.

To allow for periodic or remote monitoring, the liquefaction monitoring unit features capabilities for storing and/or transmitting data to indicate pressure, temperature, product state, temperature liquefaction margin (temperature change to cause liquefaction at constant pressure), and pressure liquefaction margin (pressure change to cause liquefaction at constant temperature). It will be appreciated that this data may be recorded or transmitted in either digital or analog form.

Liquefaction Monitoring Process

The liquefaction monitoring process of the present invention makes use of n sets of gas-specific data (n is at least equal to 1) to provide different tolerance levels regarding possible liquefaction of a gas product. These gas-specific data sets may also be referred to as reference data sets. For the purpose of illustration, 3 data sets are used in the following discussions. Each data set will contain numerical data tables and/or correlations representing data pairs that completely define different theoretical states of a gas. Specifically, the data pairs will contain values for two of these parameters: temperature, pressure, volume or a gas property that can be calculated or derived from the other parameters or thermodynamic properties such as, for example, enthalpy, entropy, density, among others. For the purposes of facilitating the description of the invention, the data sets described herein correspond to data pairs that include temperature-pressure pairs. However, it will be appreciated by those skilled in the art that using other data pairs would require one or more additional correlations to relate these other properties back to temperature and pressure.

FIG. 2 illustrates a procedure for determining the state of the gas product based on input values of two parameters or thermodynamic properties (e.g., temperature and pressure) and gas-specific reference data sets. Three reference data sets (n=1, 2 and 3) plotted as vapor pressure versus temperature are used in this illustration. These data sets are represented by curves 280, 282 and 284 respectively. Data set 1 contains highly accurate data involving saturated vapor pressure and temperature for a specific gas product. The region to the left of the curve 280 corresponds to pressure and temperature conditions under which liquefaction is occurring. Data sets 2 and 3 are used to provide or derive different liquefaction tolerance levels for the specific gas product. These tolerance level curves 282 and 284 are generally characterized by certain offsets (in the x- or y-axes) from the saturated data curve 280. Thus, the tolerance level curve 282, having smaller offsets from the saturation curve 280 than curve 284, represents pressure and temperature conditions with higher probabilities of liquefaction than those represented by curve 284. In this example, curve 282 is used to set a tolerance level for imminent liquefaction—e.g., liquefaction is likely to occur for a gas product with temperature and pressure conditions to the left of the curve 282. Curve 284 represents a tolerance level for no liquefaction—e.g., liquefaction will not occur for a gas product having temperature and pressure conditions to the right of the line 284. As shown herein, the data set number n is assigned such that the distance between a tolerance level curve for a given data set and the saturation curve 280 increases with increasing n. By comparing temperature and vapor pressure measurements for the gas product with these tolerance level curves, different liquefaction alert signals may be issued to operational personnel. Depending on specific needs for liquefaction monitoring, various factors may be used in generating these tolerance level curves. Such factors may include, for example, reference data accuracy, sensor accuracy, desired margins for liquefaction status alerts, among others.

To further illustrate the liquefaction monitoring process, five vapor pressure and temperature measurements M1, M2, M3, M4 and M5 obtained from a gas distribution system are shown in FIG. 2. Three of these measurements (M1, M2 and M3) lie within the boundary (i.e., to the left) of the tolerance level curve 282 indicating that liquefaction is imminent. For these measurements, it is assumed that some liquefaction is occurring, and a liquid warning alert is issued. If a measurement such as M4 falls between the tolerance levels of no liquefaction (e.g., curve 284) and imminent liquefaction (e.g., curve 282), a caution alert is issued to indicate a marginal vapor state—i.e., that liquefaction of the gas distribution system is imminent. Finally, for a measurement M5 outside of the tolerance level curve 284 indicating no liquefaction, an "OK" signal may be issued to indicate that the gas is in a vapor phase. For each measurement or operating point of the gas product, one can also define two parameters: pressure liquid margin (PLM) and temperature liquid margin (TLM), to represent respectively the pressure and temperature differences between the operating point and corresponding vapor pressure and temperature on the saturated data curve 280.

The liquefaction monitoring process requires an input of two parameters characterizing the operating state of the gas product, e.g., measured values for the temperature and pressure, or equivalents thereof. These input parameters can be provided by sensors such as temperature or pressure sensors that may be incorporated in the liquefaction monitor unit, existing sensors in the gas distribution system, or manual input of parameters derived from other measured properties. Product volume and other derived properties can also be used as input parameters. The process would then include additional steps to correlate these parameters back to temperature and pressure in order to compare with the tolerance level curves. For each operating state, a liquefaction tolerance check is performed to compare the input temperature and pressure values with the respective tolerance level curves. If an operating state lies outside the boundary of a given tolerance level curve representing a certain data set, the operating state is said to have passed the liquefaction tolerance check with respect to that tolerance level or data set. Thus, if a certain operating state passes a liquefaction check corresponding to a given data set, it will by definition pass all lower data sets.

Based on n sets of data, a liquefaction monitoring unit 100 is described below for implementing the liquefaction monitoring process. The liquefaction monitoring unit 100 includes, among others, software such as a tolerance-level-determination engine 102 in which the tolerance level of the gas is determined and a results-reporting engine 104 that outputs the results from the tolerance-level-determination engine 102. The process described herein may generally be implemented by a variety of microprocessors or computers, and the software may reside in various computer-readable media. The data collectors 28 of FIG. 1 may be included as part of the liquefaction monitoring unit 100, or may be operated remotely, in which case the engines 102, 104 would need to be operated for each of the data collectors 28. It will be appreciated by those skilled in the art that although certain pressure and temperature values are referred to as being "calculated" they can either be determined from a particular equation or extracted from a data table structure, such as a look-up table.

1. Tolerance-Level-Determination Engine

Figure 3:
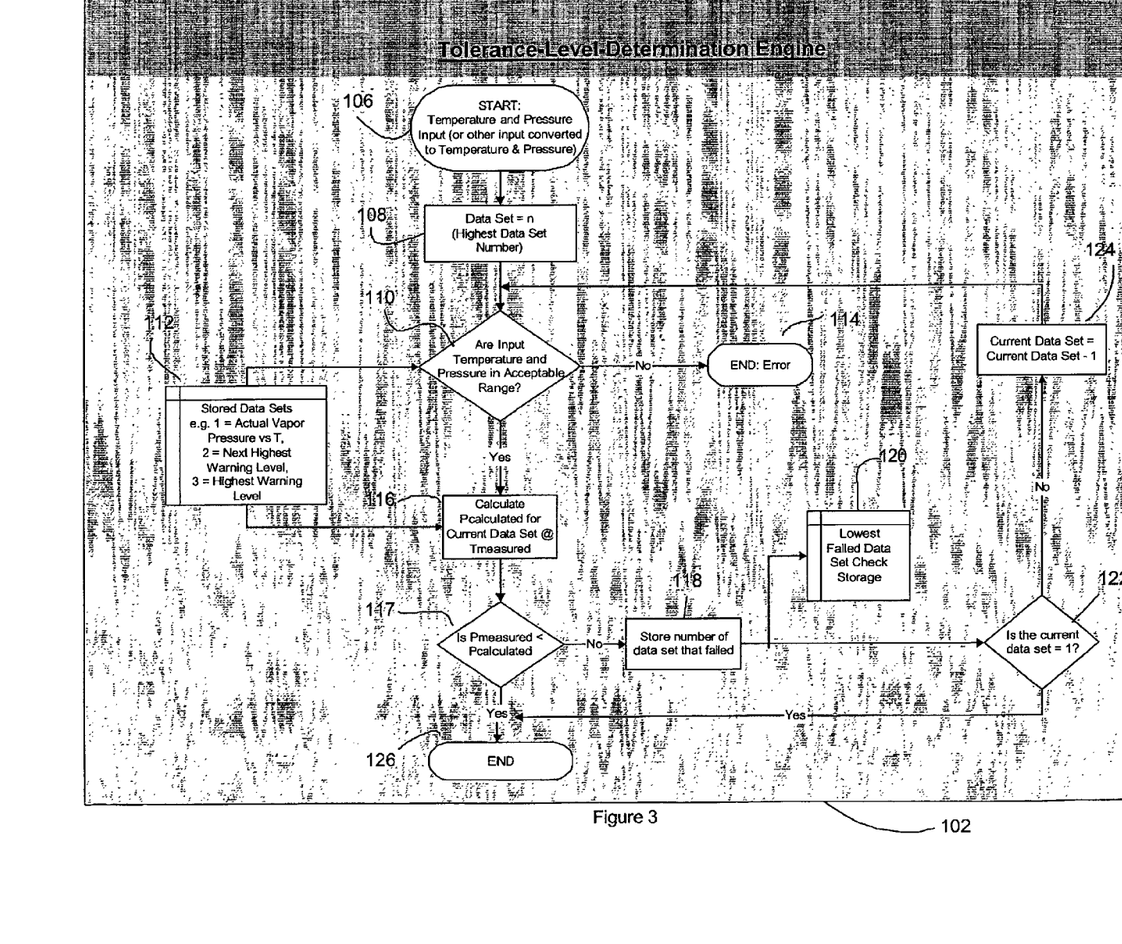
FIG. 3 is a flowchart for a tolerance-level-determination engine according to the present invention.

FIG. 3 is a flowchart for a tolerance-level-determination engine 102 for determining the status of a gas product with respect to various liquefaction tolerance levels. The tolerance-level-determination engine 102 starts initialization at step 106, which indicates that there has been no failure of liquefaction tolerance check with respect to any of the reference data sets n, and obtains input parameters or temperature and pressure data from the data collectors. If different input parameters such as volume or other thermodynamic properties are provided, these values will be correlated (e.g., using known relationships between the thermodynamic properties and temperature and pressure) to corresponding input temperature and pressure to allow subsequent comparison with the reference data sets. The n data sets may be stored in a memory or storage location 112 provided in the liquefaction monitoring unit 100. Next, at step 108, a data set pointer assigns data set 'n' as the current data set, which is represented by the tolerance level curve furthest from saturation conditions. For example, data set 'n' may correspond to data set 3 (represented by curve 284) illustrated in FIG. 2. For a given product gas, there is an acceptable range of temperature and pressure values (defined by minimum and maximum temperatures and pressures) within which the data sets are considered "valid". These minimum and maximum values are predetermined from either critical points or triple points of the gases, experimental data availability, regulatory codes and requirements, properties of construction materials (e.g. sensors, tubing), safety factors and typical operating conditions. At step 110, an inquiry is made as to whether the input or measured values are within the acceptable range of temperature and pressure. If the answer is no, an error will result and the process will be terminated at step 114. Otherwise, using the pressure and temperature relationship for the current reference data set, a pressure ($P_{calc.}$) corresponding to the input or measured temperature to the process is calculated at step 116. The relationship between $P_{calc.}$ and the input parameters is illustrated in FIG. 2, which shows an operating state 285 for a gas product with an input temperature $T_m$ and input pressure $P_m$. After $T_m$ and $P_m$ have been confirmed to be valid, $P_{calc.}$ is calculated from the current reference data set 3 (or tolerance level curve 284), at temperature $T_m$.

At step 117, the calculated pressure is compared with the input or measured pressure ($P_m$). If the input or measured pressure is lower than the calculated pressure, then the product passes the liquefaction check for the current data set, in which case the process for tolerance-level-determination engine 102 ends and the results-reporting engine 104 is initiated. If the input or measured pressure is greater than or equal to the calculated pressure, then the liquefaction check with respect to the current data set has failed, and the tolerance-level-determination engine 102 proceeds to step 118. At step 118, the data set number corresponding to the failed liquefaction check is stored in memory or storage location 120 as a lowest failed data set. Then at step 122, an inquiry is made to determine whether the current data set being operated on is data set 1. If the current data set is 1, then the process for the tolerance-level-determination engine 102 ends and the results-reporting engine 104 is initiated. If the current data set is not data set 1, then the tolerance-level-determination engine 102 proceeds to step 124 and the data set pointer decreases the current data set number by one. For example, the first time this step 124 is reached, the next data set will be n−1. The engine 102 then returns to step 110, and the liquefaction check continues with respect to the remaining data sets.

2. Results-Reporting Engine

Figure 4:
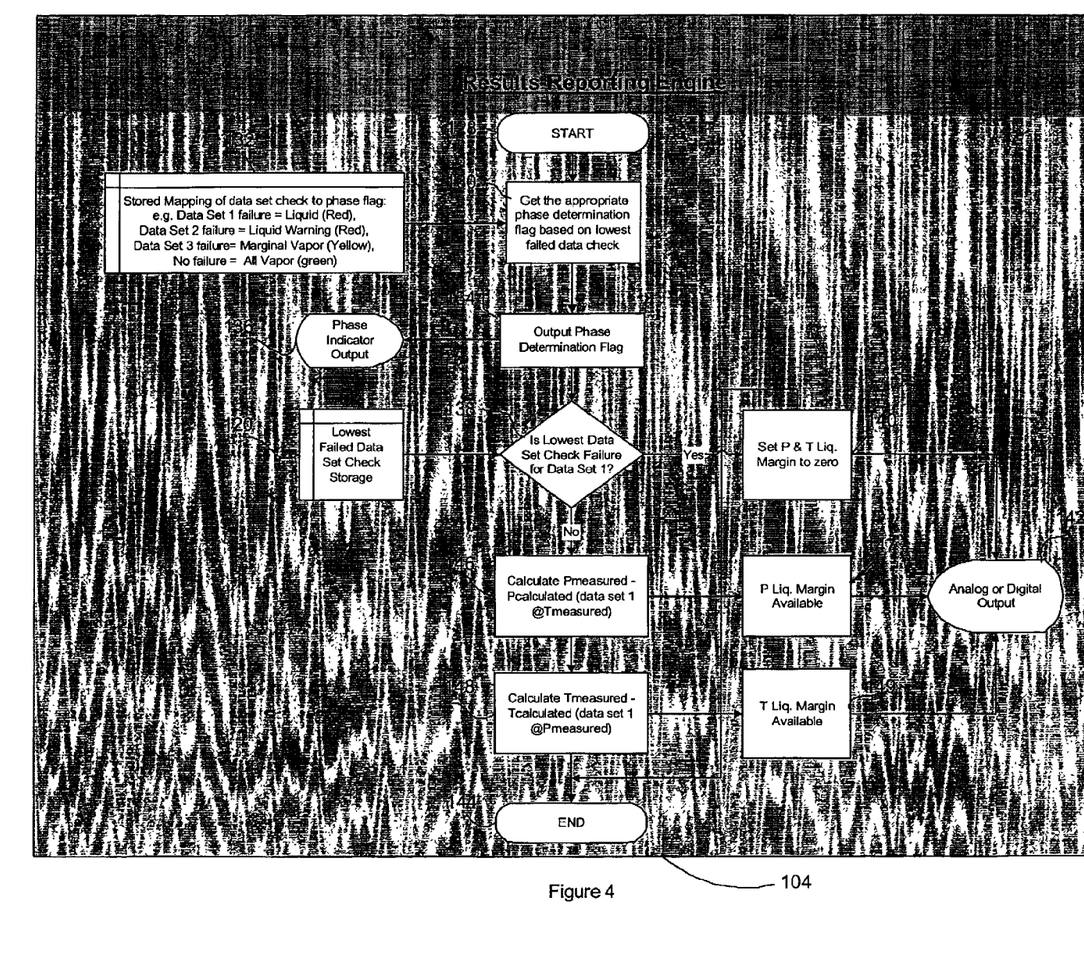
FIG. 4 is a flowchart for a results-reporting engine according to the present invention.

Results provided by the tolerance-level-determination engine 102 are reported by the results-reporting engine 104 to the operational personnel. FIG. 4 shows a flowchart for the results-reporting engine 104, which is initiated at step 128 upon termination of the process in the tolerance-level determination engine 102. At step 130, the results-reporting engine 104 first gets a phase determination flag corresponding to the lowest failed data set stored in step 118 of the tolerance-level-determination engine 102. The phase determination flag is retrieved from a memory or storage location 132, which stores a mapping of phase determination flags and corresponding results in the liquefaction checks. The phase determination flags are used to indicate the liquefaction status for the gas product. For example, if data set 1 is the lowest data set corresponding to the failed liquefaction check, then a phase determination flag indicating "Liquid" will be retrieved. If the liquefaction check has failed with respect to data set 2 or data set 3, then a phase determination flag "Liquid Warning" or "Marginal Vapor" will be retrieved respectively. On the other hand, if there is no liquefaction failure with respect to any of the data sets, then a phase determination flag indicating "all vapor" will be retrieved. The appropriate phase determination flag is then generated at step 134 and output to a phase indicator at step 136. The phase indicator output signal may be in the form of an audio or visual signal or may contain both.

Next, at step 138, an inquiry is made to determine if the lowest data set corresponding to a failed liquefaction check (stored in memory or storage location 120) is data set 1. If yes, then there are no liquefaction margins and a value of zero is given as outputs for Pressure and Temperature Liquefaction Margins at step 140. The zero value is reported to an analog or digital output at step 142. The analog or digital output may provide the results to a display on the outside of the data collector, to a display remote from the data collector or provided with a time stamp and stored either with the data collector or in a remote location. The results-reporting engine 104 then terminates at step 144. If the answer to the inquiry at step 138 is no, i.e., if the lowest data set corresponding to a failed liquefaction check is not data set 1, the results-reporting engine 104 proceeds to step 146. At step 146, the Pressure Liquefaction Margin (PLM) is calculated. The PLM is defined as the absolute value of the pressure calculated using the pressure vs. temperature correlation for data set 1 (saturated conditions) at the input temperature minus the input pressure. The resulting value, which represents the change in pressure at constant temperature that would cause liquefaction, can be provided as digital or analog output at step 147. Next, the Temperature Liquefaction Margin (TLM), which is defined as the absolute value of the temperature calculated using the pressure vs. temperature correlation for data set 1 at the measured pressure minus the input temperature, is calculated at step 148. The resulting TLM value, which represents the change in temperature at constant pressure that would cause liquefaction, can be provided as digital or analog output at step 149. The results-reporting engine 104 then terminates at step 144.

Liquefaction Monitoring Unit

Figure 5:
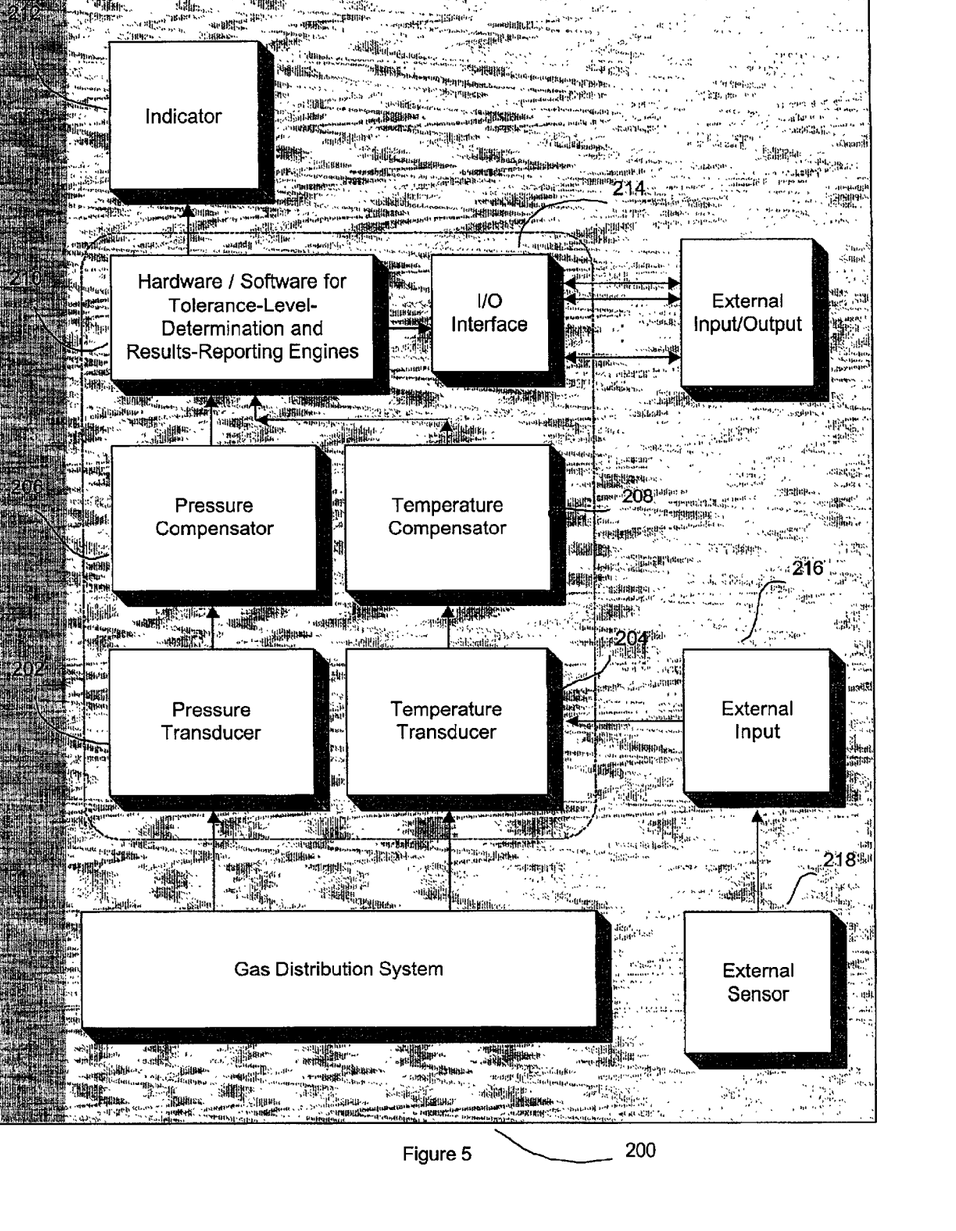
FIG. 5 is a functional block diagram of a liquefaction-monitoring unit according to the present invention.

In a preferred embodiment, the data collector 28 (of FIG. 1) is incorporated into a liquefaction monitoring unit that includes pressure and temperature sensors, the tolerance-level-determination engine and results-reporting engine in a self-contained unit. The unit preferably runs on 10–30 VDC so that it does not require its own power supply, but will be powered from a facility's existing current loop for other transducers and 4–20 mA devices. The baseline liquefaction monitoring unit preferably provides digital output, but 4–20 mA analog output may also be provided. FIG. 5 is a functional block diagram of a liquefaction monitoring unit according to one embodiment of the invention. The liquefaction monitoring unit 200 shown in FIG. 5 includes, but is not limited to, a pressure transducer 202, which is a sensor that can suitably measure pressure from as low as 0 psi(a) to as high as 60,000 psi(a) and converts it to an electrical signal output from 4 to 20 mA or from –10 to 10 VDC. Examples of devices of the type suitable for this purpose include Model TJE manufactured by Sensotec of Columbus, Ohio, USA, ThruTube® supplied by Millipore of Bedford, Mass., USA and SolidSense™ pressure transducers manufactured by Millipore of Bedford, Mass., USA. The liquefaction monitoring unit 200 also includes temperature sensor 204 such as a thermocouple or resistance temperature detector, which is located in the gas flow stream and can suitably measure temperature from as low as –196° C. to as high as 2300° C. and convert it to an electrical signal output from 4 to 20 mA or from –10 to 10 VDC. Examples of devices of the type suitable for this purpose are Model IRCO, Model GJQIN, and Model JMTSS manufactured by Omega of Stamford, Conn., USA. The sensor 202 connect to pressure sampling/temperature compensation circuit 206, or a pressure compensator, which is of the type that may include any supplementary component that is used to minimize sources of pressure error in the pressure sensor 202 caused by changing temperatures. A temperature sampling/junction compensation circuit 208, or temperature compensator, is of the type that may include any supplementary component that is used to minimize sources of temperature error in the temperature sensor 204 caused by changing temperatures. An example of such a device is a cold junction compensation module for a thermocouple that corrects an input temperature voltage for a thermal electromotive force (emf) generated by the connection of the thermocouple wires to the liquefaction monitor measurement circuits. This compensation module detects the local temperature at the thermocouple/measurement circuitry interface (reference junction) and adds the non-zero temperature of this junction to the thermocouple emf.

Where the liquid monitoring unit 200 is operated in a stand alone mode and/or networked, hardware and/or software 210 for the tolerance-level-determination engine 102 and results-reporting engine 104 are configured to handle phase determination, data comparison and data storage (which may include an intelligent data processing unit that receives measured values of pressure from sensor 202 and temperature from sensor 204). Programs in the liquefaction monitoring unit 200 are executed to perform data retrieval, calculations and data comparisons such as those outlined in FIGS. 3–4. Data comparison between input parameters characterizing the operating state and the saturated data of the gas product allows the liquid monitoring unit 200 to determine and store the following:

The "Temperature Liquefaction Margin" (TLM), which is the difference between the measured temperature and the saturated vapor temperature at the measured pressure.

The "Pressure Liquefaction Margin" (PLM), which is the difference between the measured pressure and the saturated vapor pressure at the measured temperature.

Based on the magnitude of these liquefaction margins, the physical state of the product is determined. At the extremes, the liquid monitoring unit 200 will indicate if the gas distribution system is operating safely (all vapor phase) or if there is any liquid present (two-phase or 100% liquid phase). Any number of phase indicators based on intermediate liquefaction tolerance levels can be established as needed.

Indicators 212 are included on the outside of the liquefaction monitoring unit 200 and may include an audio device, visual device or both. The indicators 212 receive inputs from the results-reporting engine and generate one or more indications such as colored lights, blinking signals, or patterned beeps on the outside of the liquefaction monitoring unit 200 to provide continuous visual and/or audio indication of the current product state. A visual/audio indicator (not shown) will also activate if the liquefaction monitoring unit 200 is malfunctioning. Digital or analog output will provide the following information for use with local and/or distributed monitoring and control systems:

a) Pressure;
b) Temperature;
c) Temperature Liquefaction Margin;
d) Pressure Liquefaction Margin;
e) Product State; and
f) Time and Date stamp.

An electrical Input/Output module 214 provides interfaces for an external input/output of data with an existing communication network having a computer monitoring station. Information relating to several liquefaction monitoring units placed discretely along the piping system is then monitored collectively by the computer monitoring station. It will further be appreciated that by monitoring the piping system at discrete points, liquefaction-monitoring data can be estimated at points along the gas piping system where it is not convenient to connect a monitoring unit.

The liquefaction monitoring unit 200 may further include a connection jack (not shown) for receiving an external temperature sensor input connector 216, which can be used to connect to an external temperature sensor 218. In some cases, the use of an external temperature sensor may result in a reduced cost for the liquefaction monitoring unit 200, e.g., if an existing temperature sensor is already available with the gas piping system. In other cases, the use of an external temperature sensor may be required due to material compatibility concerns with the gas products. If an external temperature sensor 218 is connected to the liquefaction-monitoring unit 200, this sensor overrides any internal temperature sensor that may be present—i.e., the temperature measured by the external sensor 218 will be used as an input temperature to the liquefaction monitoring process. It is also possible to use an external pressure sensor, such as one already available with the gas distribution system, to provide input pressure values to the liquefaction monitoring process.

Modifications and Variations

The liquefaction monitor process is gas-specific. Although the above discussion focuses on the use of 3 data sets to provide corresponding liquefaction tolerance levels, it is understood that other variations to the process may involve less than 3 data sets or more than 3 data sets. For example, the use of one data set (e.g., saturated data) may suffice in situations in which all that is required is an indication of safe operation (all vapor phase) or if liquid phase is present. In other situations, especially when sensitive or hazardous gases are involved, it is preferable that more than 3 data sets be used in order to provide additional liquefaction tolerance levels for appropriate warnings or alerts to be issued to operational personnel. An example of a hazardous gas that can benefit from the use of increased data sets in the liquefaction monitoring process is chlorine trifluoride.

It is understood that the implementation steps of the liquefaction monitoring process, e.g., according to the flow-charts of FIGS. 3–4, are meant for illustrative purpose only, and other variations in the process steps may also be acceptable. For example, it is possible that more than two parameters be used as inputs to the liquefaction monitoring process, although two parameters (one being correlated with temperature and the other with pressure) will suffice. It is also anticipated that different numbers of reference data sets or tolerance curves can be stored or pre-programmed within the monitoring unit. It is further possible that only a subset of these stored reference data sets be used to determine the liquefaction status of a gas product. Depending on the specific applications, units can also be configured to contain appropriate reference data sets for different gas products, for example, via plug-in memory boards, to provide necessary alert signals for the gas products. The tolerance-level-determination and the result-reporting engines may be stored in the liquefaction monitoring system in different manners, e.g., in different processors or embedded memories, or they may also be combined as a single liquefaction monitoring engine stored on one computer chip.

In another variation, liquefaction monitoring may be implemented by using a liquefaction monitoring add-on unit, which includes the tolerance-level-determination engine, results-reporting engine and other hardware and software necessary for interfacing with external components such as pressure or temperature sensors. The use of such an add-on unit has the advantage of making use of existing pressure sensors in a gas distribution system for pressure input. An external temperature sensor is also required for this configuration. This configuration may further be altered to include a data communication line in which the add-on unit may remotely monitor one or more existing pressure sensors.

Figure 6A:
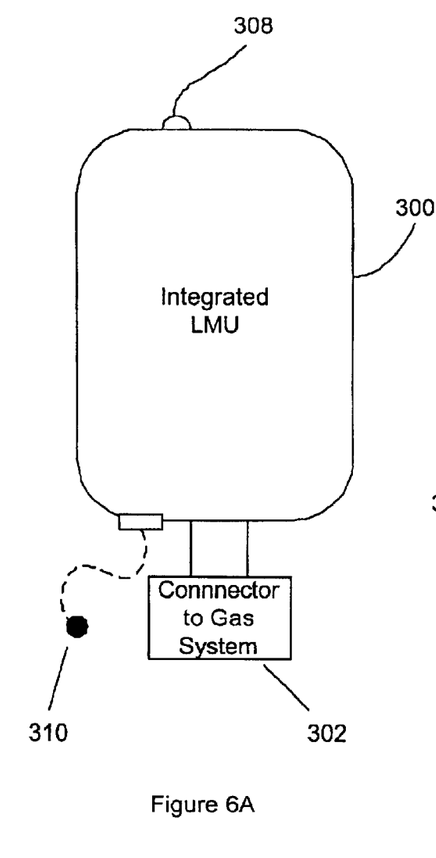
FIGS. 6A and 6B are embodiments of the liquefaction-monitoring unit of FIG. 5 having different piping connections.
Figure 6B:
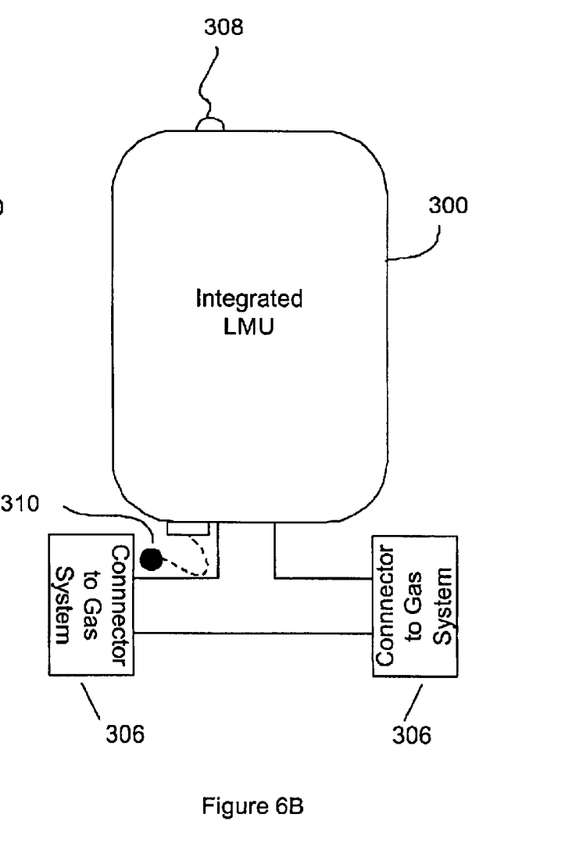

FIGS. 6A and B show two alternative configurations for connecting a liquefaction monitoring unit 300 to a gas distribution system. FIG. 6A illustrates the liquefaction monitoring unit 300 with a dead-ended connection 302 to a gas distribution system. FIG. 6B illustrates the liquefaction monitoring unit 300 connected to a gas distribution system via connectors 306 in a flow-through configuration. Both configurations have the circuitry shown in FIG. 5 and include an indicator 308 and optional external temperature sensor 310.

Figure 7:
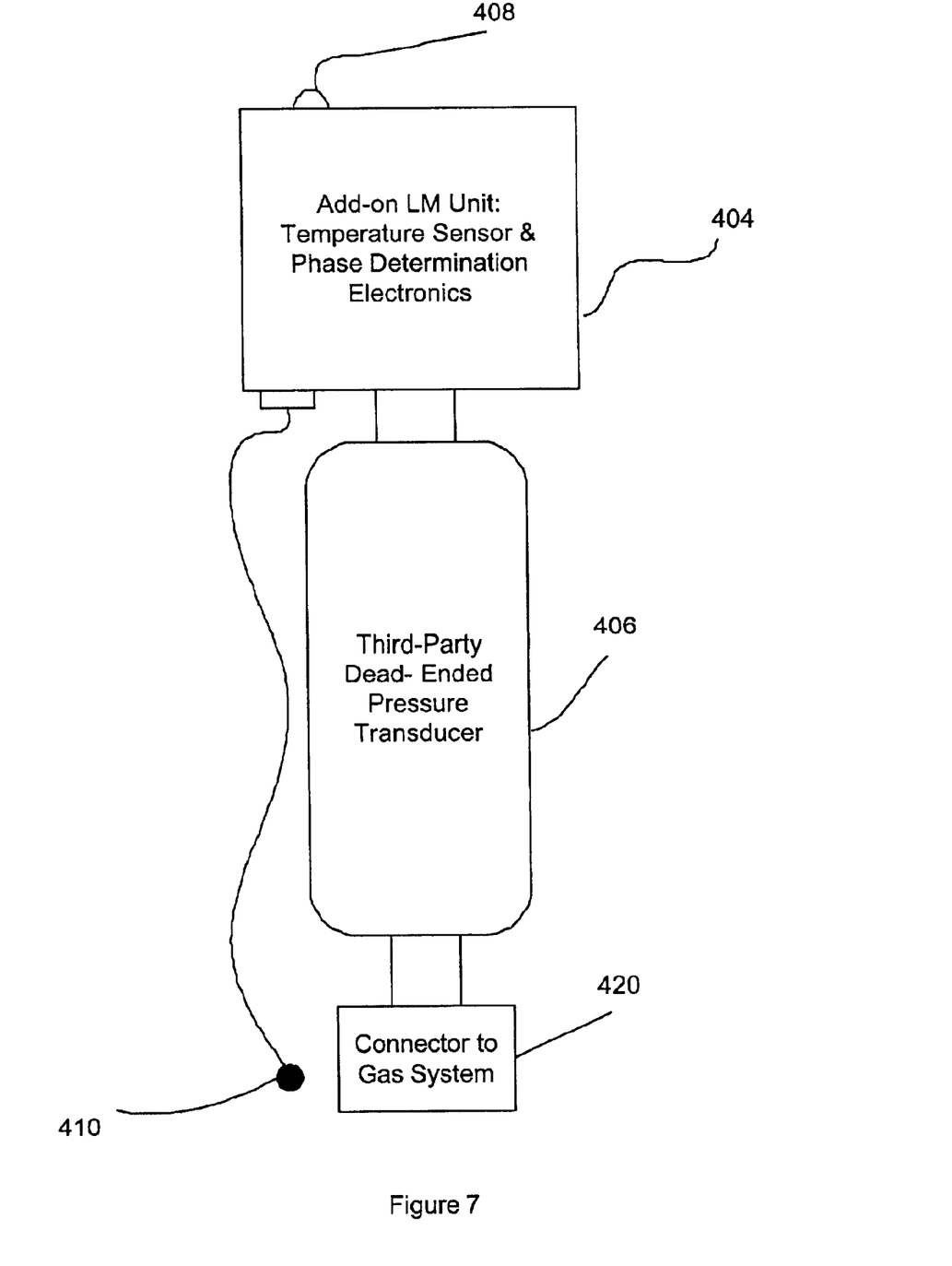
FIG. 7 is another embodiment of the liquefaction-monitoring unit of FIG. 5 illustrating an add-on version.

FIG. 7 shows another configuration involving an add-on liquefaction monitoring unit. The liquefaction monitoring add-on unit 404 is generally smaller than an integrated unit, and can be attached to any existing pressure transducer 406 in the gas distribution system. This add-on version includes all elements of the base design (shown in FIG. 5), except for the pressure sensor and associated pressure compensation circuitry. Although the liquefaction monitoring unit 404 is shown with a dead-end connector 420 to the gas system, it may also be used in a flow-through configuration. The add-on liquefaction-monitoring units 404 also includes an indicator 408 for indicating one or more process parameters, liquefaction margins or other desired, and an optional external temperature sensor 410.

Those skilled in the art of gas piping system design will appreciate that different designs will be used for different types of process gases. For example, the materials of construction will be different for corrosive vs. inert gas products, and highly toxic gases will have a dual-containment option. The base unit will have three indication levels: gas phase (green), marginal (yellow) and liquid present (red), but for more sensitive gas products, additional levels of warning may be used. The output can be 4–20 mA or digital (base design).

It is understood that the above description and drawings are illustrative of the present invention and details contained therein are not to be construed as limitations on the present invention. Changes in procedure and structure may be made

11 without departing from the scope of the present invention as defined in the following claims.

What is claimed is:

1. A system for liquefaction monitoring of a gas characterized by an operating temperature and an operating pressure in a gas piping system, comprising:
    means for providing at least two parameters of said gas;
    means for providing at least one reference data sets of said gas, said at least one reference data sets containing data pairs of temperatures and pressures;
    means for determining a liquefaction status of said gas based on said two parameters and said at least one reference data set; and
    means for reporting said liquefaction status.

2. The system of claim 1, wherein one of said at least two parameters is correlated to said operating temperature and another one of said at least two parameters is correlated to said operating pressure of said gas.

3. The system of claim 1, wherein said means for providing at least two parameters comprises at least one sensor selected from the group consisting of a temperature sensor and a pressure sensor.

4. The system of claim 1, wherein said at least two parameters are said operating temperature and operating pressure of said gas measured respectively by a temperature sensor and a pressure sensor.

5. The system of claim 1, wherein said at least one reference data sets contains data pairs of temperatures and corresponding saturated vapor pressures of said gas.

6. The system of claim 1, wherein said at least one reference data sets consists of three reference data sets, said three reference data sets giving rise respectively to three liquefaction tolerance levels, and one of said three reference data sets contains saturated data for said gas product.

7. The system of claim 6, wherein said means for determining said liquefaction status is a tolerance-level-determination engine that compares at least one of said operating temperature and said operating pressure of said gas with at least one of said three liquefaction tolerance levels to determine said liquefaction status.

8. The system of claim 7, wherein said means for reporting said liquefaction status of said gas is a results-reporting engine that reports said liquefaction status, and further calculates and reports at least one of a pressure liquefaction margin and a temperature liquefaction margin for said gas.

9. A system for liquefaction monitoring of a gas product in a gas piping system, comprising:
    at least one sensor selected from the group consisting of temperature and pressure sensors for monitoring said gas product;
    a tolerance-level-determination engine adapted for determining a liquefaction status of said gas product using data from said at least one sensor; and
    a results-reporting engine operatively connected to said tolerance-level-determination engine for reporting said liquefaction status.

10. The system of claim 9, wherein said tolerance-level-determination engine is adapted to receive two input parameters that are correlated respectively with an operating temperature and an operating pressure of said gas product; one of said two input parameters being provided by said at least one sensor; and said liquefaction status is determined by comparing data derived from said two input parameters and said one or more reference data sets comprising saturated temperature and vapor data for said product gas.

11. The system of claim 10, further comprising a compensation circuit selected from the group of a temperature compensation circuit and a pressure compensation circuit.

12

12. The system of claim 9, wherein said system is connected to said gas piping system by a connection selected from the group consisting of a dead-ended connection and a flow-through connection.

13. The system of claim 9, wherein said tolerance-level-determination engine comprises at least one of means for phase determination, means for data comparison and means for data storage.

14. The system of claim 9, wherein said results-reporting engine comprises at least one of means for pressure liquefaction margin determination and means for temperature liquefaction margin determination.

15. The system of claim 9, wherein said at least one sensor and said engines are enclosed within a single housing.

16. A system for use on a gas piping system having a pressure transducer comprising:
    a tolerance-level-determination engine operatively connected to said pressure transducer, and adapted to determine a liquefaction status of a gas in said gas piping system;
    a temperature data collector connected to said tolerance-level-determination engine;
    a results-reporting engine operatively connected to said tolerance-level-determination engine; and
    at least one indicator operatively connected to said results-reporting engine and adapted to indicate a liquefaction status of a gas product.

17. The system of claim 16 further comprising a housing for holding said tolerance-level-determination engine and said results-reporting engine, said housing being adapted to mount onto said gas piping system proximate to said pressure transducer.

18. A system for use on a gas piping system containing a gas product, said system comprising:
    sensors adapted to monitor a pressure and a temperature of said gas product;
    a tolerance-level-determination engine adapted for liquefaction monitoring using data from said temperature and pressure sensors;
    a results reporting-engine operatively connected to said tolerance-level-determination engine;
    a housing enclosing said tolerance-level-determination engine and said results reporting engine;
    said housing being removably connected to said gas piping system; and
    at least one indicator connected to said results-reporting engine.

19. The system of claim 18 wherein said tolerance-level-determination engine includes means for adapting tolerance-levels to different gas products.

20. The system of claim 18 wherein said housing is selectively movable along said gas-piping system.

21. The system of claim 18 wherein:
    said housing, sensors and results-reporting engine form a unit;
    said system including a plurality of units operatively positioned along said gas piping system, a communications network having a monitoring station, said monitoring station including means for monitoring said units.

22. A method of determining liquefaction of a gas product in a gas piping system using a data collector, said method comprising the steps of:

gathering data from said gas product selected from the group consisting of pressure and temperature data; and determining a liquefaction status from said gathered data.

23. The method of claim 22 further comprising the step of indicating said liquefaction tolerance level.

24. The method of claim 23 wherein said indicating step includes one of delivering said indication remotely from said gas piping system and delivering said indication at a location proximate to said gas piping system.

25. The method of claim 22 wherein said determining step includes providing theoretical saturation properties of said gas product.

26. The method of claim 25 wherein said determining step further includes comparing said gathered data to said theoretical saturation properties of said gas product.

27. A method for liquefaction monitoring of a gas in a piping system, comprising:

providing at least two parameters of said gas, said at least two parameters being correlated respectively to an operating pressure and an operating temperature of said gas;

providing a least one reference data set for said gas, said at least one reference data set containing data pairs of temperatures and pressures;

determining a liquefaction status of said gas based on a comparison of said at least two parameters and said at least one reference data set; and reporting said liquefaction status for said gas.

* * * * *